United States Patent [19]
Bonne

[11] Patent Number: 5,486,107
[45] Date of Patent: Jan. 23, 1996

[54] DETERMINATION OF FUEL CHARACTERISTICS

[75] Inventor: Ulrich Bonne, Hopkins, Minn.

[73] Assignee: Honeywell, Inc., Minneapolis, Mich.

[21] Appl. No.: 301,225

[22] Filed: Sep. 6, 1994

Related U.S. Application Data

[63] Continuation of Ser. No. 828,135, Jan. 30, 1992, abandoned.

[51] Int. Cl.$^6$ ........................................ F23N 5/00
[52] U.S. Cl. ........................ 431/12; 431/2; 431/89; 431/90; 364/557; 374/43
[58] Field of Search ............... 73/25.03, 204.11; 364/557, 556; 374/43; 431/2, 13, 12, 18, 89, 90

[56] References Cited

U.S. PATENT DOCUMENTS

| | | |
|---|---|---|
| 4,359,284 | 11/1982 | Kude et al. . |
| 4,944,035 | 7/1990 | Aagardl et al. . |
| 4,956,793 | 9/1990 | Bonne et al. . |
| 4,961,348 | 10/1990 | Bonne . |
| 4,993,222 | 2/1991 | Iwai et al. ........................ 431/12 X |
| 5,177,696 | 1/1993 | Bonne ................................ 364/557 |
| 5,187,674 | 2/1993 | Bonne ................................ 364/558 |
| 5,220,830 | 6/1993 | Bonne ............................. 73/204.21 |
| 5,235,844 | 8/1993 | Bonne et al. ..................... 73/24.01 |
| 5,303,167 | 4/1994 | Bonne ................................ 364/556 |
| 5,311,447 | 5/1994 | Bonne ................................ 364/509 |

FOREIGN PATENT DOCUMENTS

| | | |
|---|---|---|
| 0348244 | 12/1989 | European Pat. Off. . |
| 0439950 | 8/1991 | European Pat. Off. . |
| 9106809 | 5/1991 | WIPO . |

*Primary Examiner*—Carl D. Price
*Attorney, Agent, or Firm*—John G. Shudy, Jr.

[57] ABSTRACT

A method of determining thermophysical or thermochemical parameters of a fuel gas is disclosed which has wide application both as to applicable fuels and applicable parameters. A relationship has been discovered that allows the determination of many parameters based on a basic relationship with the characteristic specific heat and thermal conductivity at a reference condition of the fuel gas and the rate of change of these characteristics at the reference conditions.

26 Claims, 6 Drawing Sheets

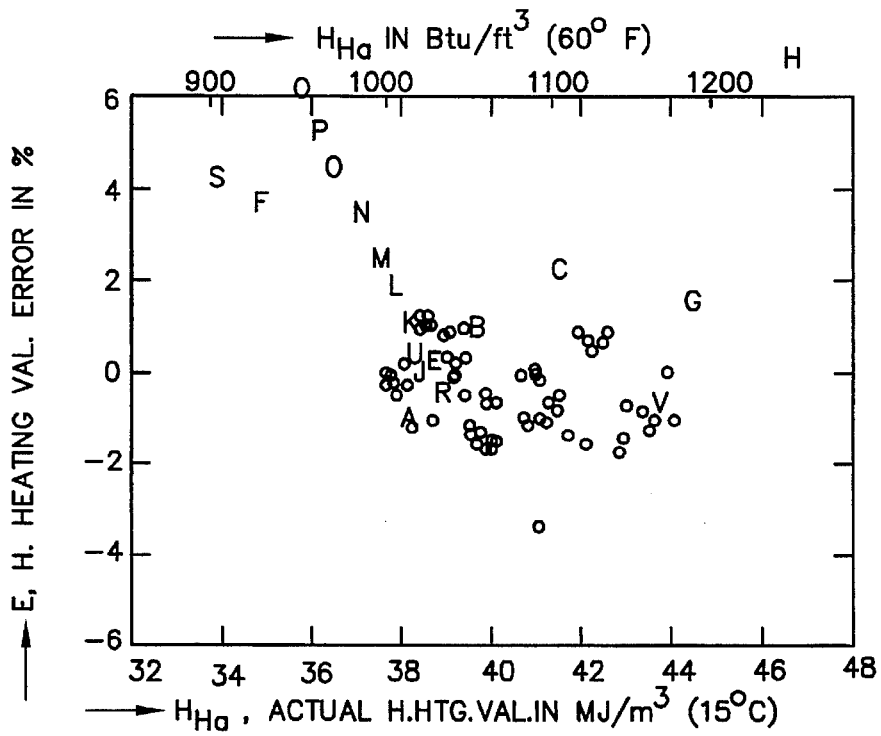
FIG. 3 COMPARISON BETWEEN ACTUAL AND COMPUTED HEATING VALUE OF GASES
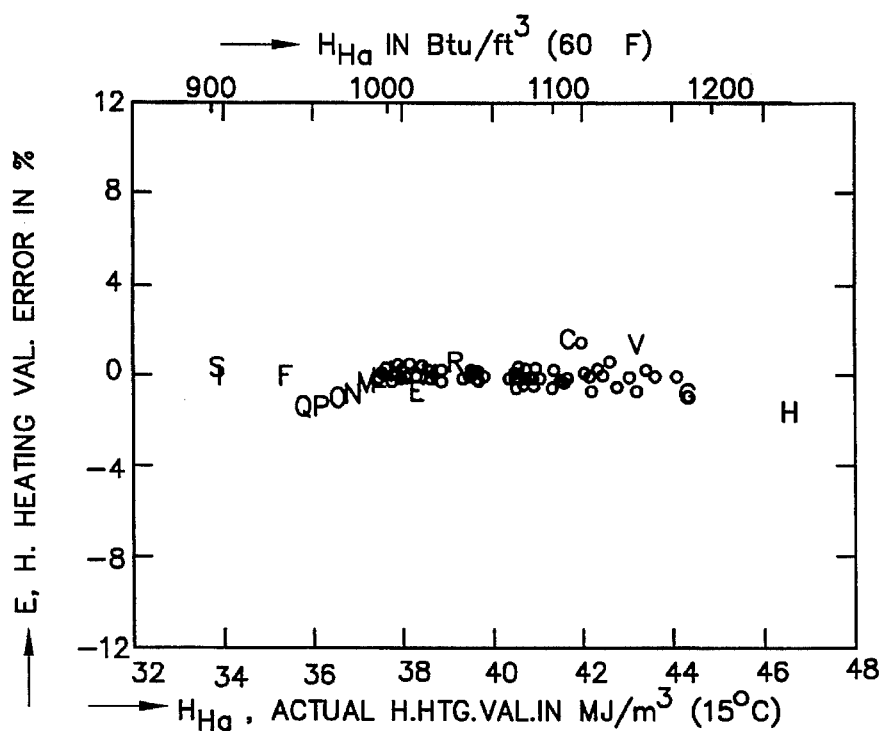
FIG. 4 COMPARISON BETWEEN ACTUAL AND COMPUTED HEATING VALUE OF GASES

VISCOSITY DETERMINATION ERROR
FOR NATURAL GASES.

DETERMINATION OF FUEL CHARACTERISTICS

This application is a continuation of application Ser. No. 07/828,135, filed Jan. 30, 1992, abandoned.

BACKGROUND OF THE INVENTION

I. Cross Reference to Related Materials

Previously assigned patents contain information relating to the determination of certain physical parameters with respect to fuels of interest in the present application. These include:

U.S. Pat. No. 4 944 035 entitled MEASUREMENT OF THERMAL CONDUCTIVITY IN SPECIFIC HEAT which issued on Jul. 24, 1990 to Roger L. Aagard, Ulrich Bonne, the inventor in the present application, and Robert J. Matthys;

U.S. Pat. No. 4 956 793 which issued Sep. 11, 1990 to Ulrich Bonne, the inventor in the present application, and Steven D. James;

U.S. Pat. No. 4 961 348 issued Oct. 9, 1990 to Ulrich Bonne, the inventor in the present application, entitled FLOW METER FLUID COMPOSITION CORRECTION;

Ser. No. 07/285,890 filed Dec. 16, 1988 entitled LAMINARIZED FLOW METER;

Application Ser. No. 07/789,411 filed Nov. 1, 1991, which is a continuation of application Ser. No. 07/429,138 filed Oct. 30, 1989 to Ulrich Bonne, the inventor in the present application.

To the extent necessary for the complete description of any aspect of the present application, material from the above may be deemed incorporated by reference into this application.

II. Field of the Invention

The present invention is directed generally to combustion control and, more particularly, to the improved determination of fuel characteristics including heating value and oxygen demand and Wobbe Index or Number which can be utilized for more accurate fuel metering and combustion control (i.e. efficiency and firing rate) in terms of accurately determining the amount of oxygen needed for complete combustion for a given type and amount of fuel which is valid for a wide range of fuel compositions and more accurate inasmuch as it is less sensitive to errors in the measured parameters from which the values are derived.

III. Description of the Related Art

The determination of the oxygen demand and heating value, energy content or heat of combustion of a fuel represents an important determination with respect to both the operation of a combustion system with respect to proper combustion of the fuel and in determining the quantitative commercial value of the fuel with respect to the supplier. In this regard, various methods for measuring the heat available from fuel gases have been implemented and used for many purposes. As evidenced by the above-referenced patents, the use of spaced microscopic heating and sensing elements on semiconductor chips to measure certain physical parameters in gaseous media is known. These "microbridge" system are extremely fast reacting, very stable and very sensitive with respect to measuring thermally induced changes in electrical resistance when placed in a fluid of interest. The use of such devices to accurately determine thermal conductivity, k, and specific heat are shown in Aagard, et al., above, and Bonne, et al. '793, also cited above, also enables the accurate determination of specific gravity of a species of interest.

The related application, Ser. No. 07,789,411 filed Nov. 1, 1991, discloses the use of k and $c_p$ for a determination of heating value or heat of combustion, H, which is, in turn, used for the determination and control of the delivered energy and the oxygen demand to control the efficiency or fuel-to-air ratio in a metering and/or combustion system, respectively. All determinations of Y=H or D or Wo for a given type and amount of fuel or the oxygen demand of the fuel, D, were correlated to k and $c_p$. The relationship utilized in the above cross-referenced application Ser. No. 07/789, 411 was written in terms of a direct relation of thermal conductivity, k, and specific heat, $c_p$, as measured for flowing fuel and evaluated according to the following polynomial relationship:

$$H = A_1 f_1^{n1}(x) \cdot A_2 f_2^{n2}(x) \cdot A_3 f_3^{n3}(x) \qquad (1)$$

where $A_1, A_2, A_3$=constant coefficients n1, n2, n3=exponents $f_1(x)$=k (thermal conductivity at a first temperature)

$f_2(x)$=k (thermal conductivity at a second temperature)

$f_3(x)$=$c_p$ (specific heat determined at one temperature, normally the temperature of $f_1(x)$ or $f_2(x)$).

Results obtained utilizing the relationship of equation 1 for a selection of over 60 natural gases was used to obtain empirical constants and exponents, and these, in turn, were applied to later determinations of different fuels. The results obtained utilizing equation 1 with the empirically derived constants and exponents have proved to be generally quite satisfactory calculated (error generally was <0.5%) for natural gases characterized by concentrations of carbon dioxide ($CO_2$) and nitrogen ($N_2$) not exceeding two percent (2%) by volume.

When the same equation was recently applied to an expanded range of gases notably including gases containing nitrogen levels as high as over 20% and containing much higher concentrations of ethane, propane, $CO_2$ and hydrogen, however, errors in the determination of heating value increased from less than 0.5% to over 12%. This is illustrated for 78 natural and 22 test gases in FIG. 3. Even after extensive work in readjusting the empirical coefficients and exponents of the algorithms of the equation 1, the maximum error has been found to be still over 6%. An error this large still is unsatisfactory for most uses of the higher heating value, for the purposes of substantiating amounts charged customers for the heating value of fuel supplied, or fuel-to-air ratio combustion control based on oxygen demand measurement. In this regard, any improvement which substantially reduces the error and increases the reliability of determinations of the type involved without adding a great deal of cost to the measurement apparatus would be highly desirable.

The invention presents a highly accurate on-line system for the determination of the higher heating value H by monitoring the heat content of gaseous hydrocarbon fuels on a volumetric basis. In addition, however, knowledge of another very important dimension is necessary to account for changes in the specific gravity of the fuel so that a constant heat input to a pressure fueled burner system can be maintained. Thus, for example, while utility companies are very much concerned that the customer be charged precisely for the amount of heat value sold on a volumetric basis, those utilizing the gaseous fuel are also concerned that the Wobbe Number of Index, defined below, be considered so the burner energy input remains constant, whatever the relative Btu content be on a volumetric basis. This is especially important in devices that use mass flow devices such as orifice meters to measure fuel flow to the burners. Variations in burner efficiency can be very costly especially in industrial burner applications for which we need to know oxygen demand of the fuel in order to control the fuel/air ratio.

Accordingly, changes in the density or specific gravity of the fuel should be considered in addition to the heating value of the fuel on a volumetric flow basis in order to assure constant heat input to the burners. Such may be accomplished by determining and monitoring the Wobbe Number or Index of the fuel, Wo, which is defined as follows:

$$Wo = H\rho^{-0.5} \qquad (2)$$

where:

H=the higher heating value of the fuel in Btu's/ft$^3$ joules/meter$^3$, etc. and $\rho$=the relative density or specific gravity of the fuel.

It is apparent from the above that by considering changes in the specific gravity of the fuel gas in addition to the heating value on a standard volumetric basis, the Wobbe Index is useful as a measure of the potential heat production available for a given burner input. Thus, a fuel mixture of constant Wobbe Index will provide constant heat input to an orifice-controlled burner system. Because of the great variation in the heating value of gaseous fuels, the Wobbe Index has long been used in connection with providing a more constant firing rate input to burner systems to produce the specified performance and system stability. In the past, however, in order to determine the Wobbe Index of a fuel gas, separate calorimetry and density measurements had to be made and the results combined. This involved the use of expensive calorimeters and density meters and required considerable time to obtain useable results. It was generally not affordable to determine a representative real-time Wobbe Index on-line control in an industrial setting.

For diverse applications, the measurement or determination of thermophysical or thermochemical related properties is very desirable. These include compressibility (Z), viscosity ($\eta$), pseudocritical temperature and pressure. Other parameters or fuel properties of interest include flammability limits, critical compression ratio (i.e. the maximum compression ratio before incipient knock), flame speed, and yellow tipping of the flame. Of course, it would be very desirable if all of these parameters could also be accurately correctable to the measurable or readily determinable quantities k, $c_p$, dk/dT, d$c_p$/dT, T and P.

SUMMARY OF THE INVENTION

In accordance with the present invention, there is provided an improved method for the determination of many thermophysical and thermochemical parameters of fuel gases including but not limited to heating value or heat of combustion, H, amount of oxygen needed for complete combustion for a given type and amount of fuel, or oxygen demand, D, and additional parameters as the Wobbe Number or Index, Wo, based on new discoveries with regard to determining the relationship among the above and the thermal conductivity, k, and specific heat, $c_p$. The present invention contemplates the use of a class of relationships among these values which has been found to be valid and more accurate, for a much wider range of fuel compositions including those with large amounts of higher alkanes, hydrogen and non-combustibles. The present invention provides this accuracy in a manner which exhibits a lower sensitivity to measurement errors in obtaining k and $c_p$ and which is capable of readily presenting yield outputs which can be utilized for more than one application or usage. Unlike previous determinations, the present invention utilizes parameters which are directly measurable, are first converted to a reference condition of pressure and temperature and may not require the measurement of pressure. This has led to a new and more accurate polynomial expression of H, Wo, or D. The new, more accurate polynomial representation uses a structure leading to more accurate results.

As indicated above, while earlier expressions of H or D in terms of measured values of k or $c_p$ were accurate (i.e. <0.5% error) with respect to pure fuels or fuels having small amounts, i.e. less than about 2%, of non-combustibles such as $CO_2$ or $N_2$ at higher nitrogen levels, i.e. 20% or more, or higher concentrations of ethane, propane, $CO_2$, $H_2$, or the like, the accuracy of such determinations were subject to a great deal more error (>6% even after readjustment of the coefficients and exponents of the algorithm of equation 1.

According to the present invention, it has been found that the relationship that exists between H, Wo or D, and k and $c_p$ can be expanded to accurately cover a greater variety of fuel gases, including those containing large amounts of alkane hydrocarbons, higher than methane outside the main range of conventional fuels and containing higher amounts of other species including $N_2$, $CO_2$ and $H_2$ without sacrificing accuracy of determinations obtained with respect to the other fuel gases. In addition to greatly expanding the variety of accurately determinable fuel gases, the present invention also makes it readily possible to measure or determine other thermophysical or thermochemical related properties including compressibility (Z), viscosity ($\eta$), pseudocritical temperature ($T_{pc}$) and pseudocritical pressure ($P_{pc}$), flammability limits, critical compression ratio, flame speed and yellow tipping of the flame.

According to the present invention, it has been discovered that a generally universal correlation exists between Y, a given property of interest, and the measured microbridge properties of thermal conductivity, k, specific heat, $c_p$, temperature, T, pressure, P (which can also be independently sensed), the derivatives, dk/dT and d$c_p$/dT, and ratios $k_1/k_2$, $C_{p1}/C_{p2}$ and $C_{pv1}/C_{pv2}$.

A preferred relationship in accordance with the invention can be expressed as follows:

$$Y_s = A_0 + A_1 k_s^{n1} c_{ps}^{m1} x_s^{p1} y_s^{q1} T_s^{r1} P_s^{s1} + \\ A_2 k_s^{n2} c_p^{m2} x_s^{p2} y_s^{q2} T_s^{r2} P_s^{s2} + \ldots \qquad (3)$$

$$= \Sigma_i A_i k_s^{ni} c_{ps}^{mi} x_s^{pi} y_s^{qi} T_s^{ri} P_s^{si} \qquad (4)$$

where dependent variable, $Y_s$, represents any one of higher heating value, H; oxygen demand, D; Wobbe Index, Wo; relative density or specific gravity, $\rho$; absolute density $\rho_a$; inerts, I; compressibility factor, Z; critical compression ratio, $R_c$; viscosity, $\eta$; etc.

$A_0, A_1 \ldots A_i$ are constants or coefficients, $n_i, m_i, p_i, q_i, r_i, s_i$ are exponents of values from 20 to 20, including zero, with the number of terms, i, ranging from 1 to 15, $k_s$ and $c_{ps}$ represent their values at a predetermined condition, which could be 60° F., 0° C., 15° C. or any other arbitrarily chosen temperature and pressure, $x_s$ represents $dk/dT$ at the reference condition, $Y_s$ represents $dc_p/dT$ or $C_{pvT1}/C_{pvTs}$ at a reference condition, $T_1 \neq T_s$ (the units of $c_p$ are typically energy per unit of mass or mole and per $\Delta T$, while those of $c_{pv}$ are typically energy per volume and per $\Delta T$), $T_s$ represents temperature at said reference condition, $P_s$ represents absolute pressure at the reference condition.

A preferred method of determining $k_s$ and $c_{ps}$ may be represented by the expressions:

$$k_s = a_0 + a_1 k_{t1}^{m1} - a_2(k_{t2} - k_{t1})(T_1 - T_s)/(T_2 - T_1) \quad (5)$$

$$c_{ps} = b_0 + b_1 c_{pt1}^{n1} - b_2(c_{pt2} - c_{pt1})(T_1 - T_s)/(T_2 - T_1) \quad (6)$$

where $a_1$ and $b_1$ are constants, $m1$ and $n1$ are exponents $T_1$ and $T_2$ are temperatures or pressures in a desired range $T_s$ is the standard temperature or pressure.

This relation has been found to significantly reduce errors in $k$ and $c_p$ as follows:

1) It uses values of at least two measurements of $k$ and $c_p$ at different temperatures interpolated or extrapolated to a standard condition increase accuracy.

2) Using the ratio of values at different thermodynamic conditions allows one to make use of physical properties that are largely or more independent of such thermodynamic condition (e.g. varying the temperature at constant pressure for $c_{pvT1}/c_{pvT2}$ eliminates the pressure influence of $c_{pv}$ whereas it would not be eliminated by simply using $dc_{pv}/dT$).

3) Even more accuracy may be available if the relation is fitted individually to a series of limited ranges of parameter values which might include two or more ranges for any of the involved parameters; for example, in a simple case of two ranges of fuel gas heating values one might select $H > 1050$ Btu/ft$^3$ and $H < 1050$ Btu/ft$^3$. Thus, the $Y_s$ polynomial can then be optimized for each given range. Depending on the application, any number of relatively limited ranges can be implemented.

As more fully described in the above-referenced Bonne, et al. (U.S. Pat. No. 4 956 793) patent, the relative density, or specific gravity, $\rho$, in relation to that of air, has been found to be a function of $c_p$ and $k$ according to an empirical polynomial relationship of the form:

$$f(c_p, k_t) = a_6 + a_7 c_{pt7}^{n7} + \ldots + a_8 k_{T8}^{n8} + \ldots + a_m k_{Tm}^{nm} \quad 7)$$

where $a_6 \ldots a_m$ are constants $k_{T1} - k_{Tm}$ are thermal conductivities at subscript temperatures $T_1 - T_m$ and $n_1 - n_m$ are exponents.

The Wobbe Number can also be derived from the higher heating value, $H$, and the relative density or specific gravity, $\rho$, according to the relation given above in equation (2) or $Wo = H_{92}^{0.5}$.

BRIEF DESCRIPTION OF THE DRAWINGS

FIG. 3 is a graphical representation of a comparison between the actual and computed heating value of 78 gases (o) and 22 test gases (A-V) using a prior correlating relationship;

FIG. 4 is a graphical representation of a comparison between the actual and computed heating value of the 78 natural gases (o) and 22 test gases (A-V) of FIG. 3 using the correlating relationship of the present invention;

DETAILED DESCRIPTION OF THE PREFERRED EMBODIMENTS

Figure 1:
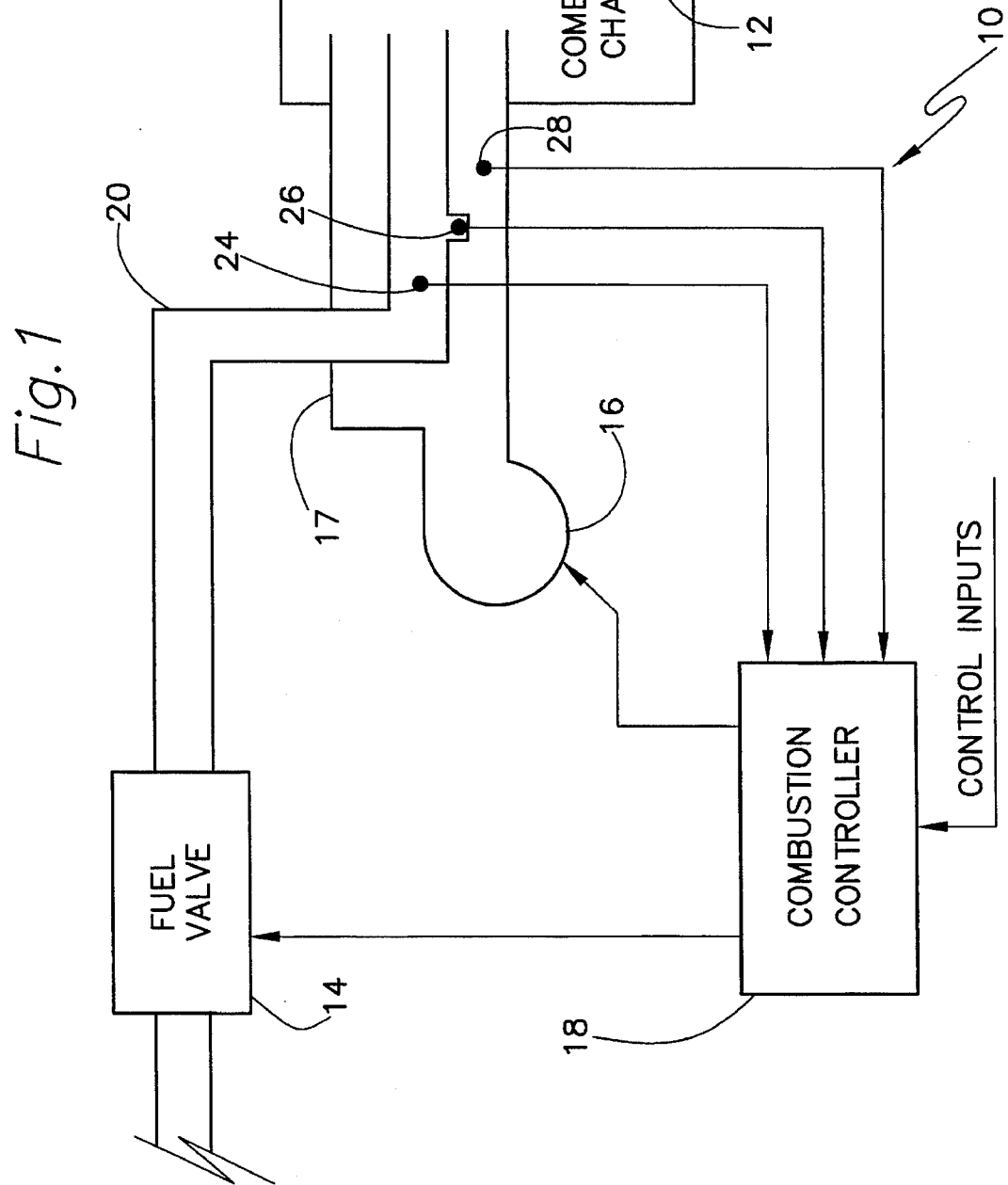
FIG. 1 is a block diagram of a combustion system.

FIG. 1 shows a block diagram of a typical combustion system generally at 10. Heating system 10 includes combustion chamber 12, fuel valves 14, air blower 16 and combustion controller 18. Fuel enters combustion chamber 12 through fuel conduit 20 where it is combined with air blown from air blower 16. The fuel and air mixture is ignited in combustion chamber 12 and resulting flue gases exit combustion chamber 12 through flue 22.

Combustion controller 18 controls the fuel-to-air mixture in combustion chamber 12 by opening and closing fuel valves 14 and by opening and closing air dampers in air conduit 17. Combustion controller 18 controls the fuel-to-air mixture based on control inputs entered by a heating system operator as well as sensor inputs received from sensors 24 and 26 in fuel conduit 20, and sensor 28 in air conduit 17.

Sensors 24 and 28 are typically microbridge or microanemometer sensors which communicate with flowing fuel in fuel conduit 20 and flowing air in air conduit 17. This type of sensor is described in more detail in the above-referenced application Ser. No. 285,890.

Sensors 24 and 28 are directly exposed to the stream of fluid flowing past them in conduits 20 and 17, respectively. Sensors 24 and 28 are used to directly measure dynamic fluid flow characteristics of the respective fluids. Sensor 26, while in contact with the fuel gas, is recessed in a dead-ended cavity and not exposed to direct flow.

Figure 2:
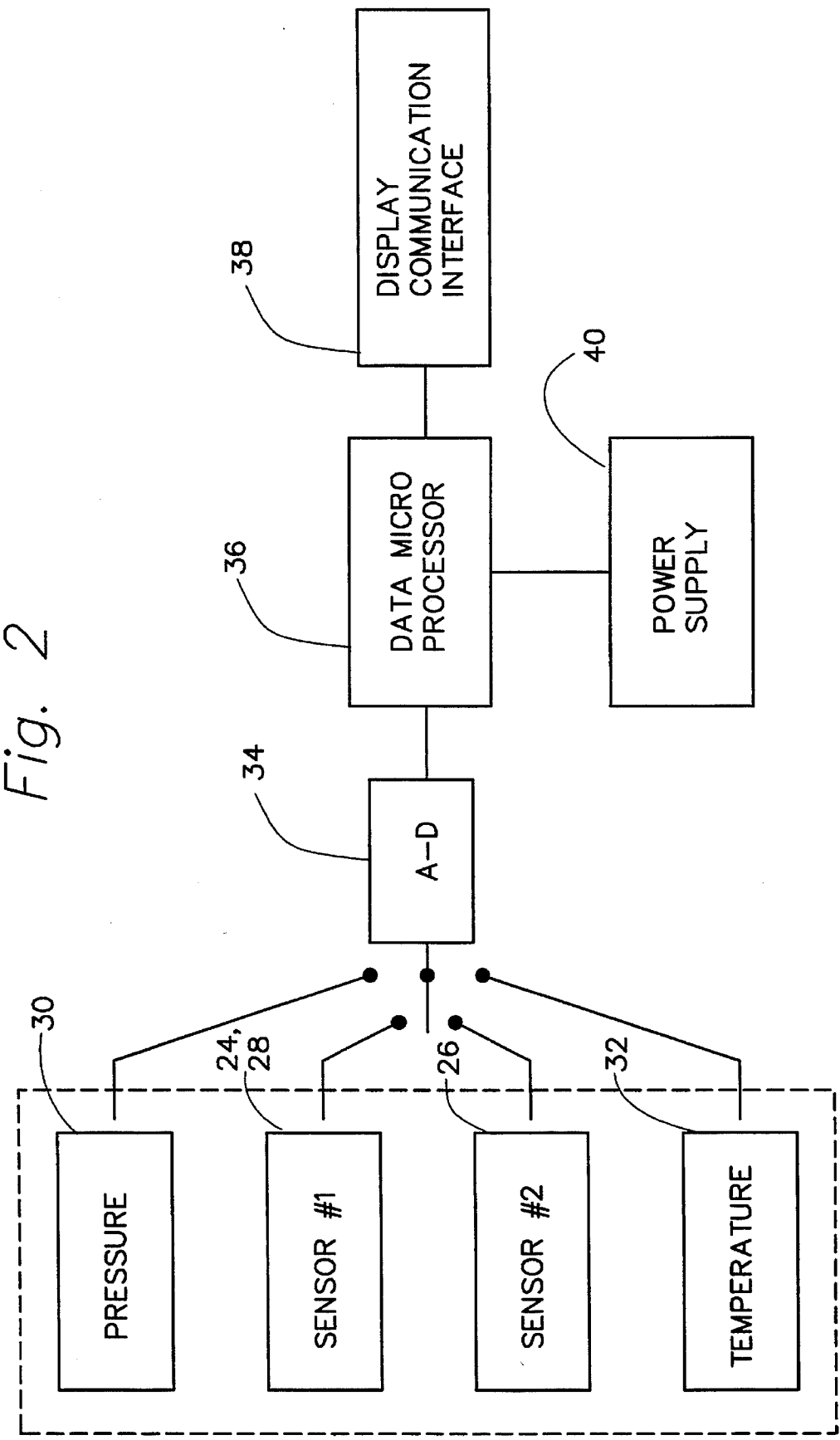
FIG. 2 is a block diagram of the sensing and signal processing system of the invention.

FIG. 2 shows a block diagram of the sensing and signal processing system of the invention which may be associated with the combustion system of FIG. 1. It includes the dynamic or exposed microbridge flow sensors 24 and 28 together with static microbridge 26. In addition, an optional pressure sensor 30 and a temperature sensor 32 are provided. The output of these devices is fed as an input to an analog to digital (A/D) converter 34 which provides input to a data processing device such as a data microprocessor 36. Display and output devices which may take any form which would occur to those skilled in the art is shown at 38. A power supply for the system is depicted by 40.

Microbridge sensor 26 enables other parameters of the fuel to be measured simultaneously with the dynamic flow. Sensor 26 can be used for the direct measurement of thermal conductivity, $k$, and specific heat, $c_p$, in accordance with a technique which allows the accurate determination of both properties. That technique contemplates generating an energy or temperature pulse in one or more heater elements disposed in and closely coupled to the fluid medium in conduit 20. Characteristic values of k and $c_p$ of the fluid in conduit 20 then cause corresponding changes in the time variable temperature response of the heater to the temperature pulse. Under relatively static fluid flow conditions this, in turn, induces corresponding changes in the time variable response of more temperature responsive sensors coupled to the heater principally via the fluid medium in conduit 20.

The thermal pulse need be only of sufficient duration that the heater achieve a substantially steady-state temperature for a short time. Such a system of determining thermal conductivity, k, and specific heat, $c_p$, is described in greater detail in above-referenced patents 4 956 793 and 4 944 035.

It has also been found that once the specific heat and thermal conductivity of the fluid have been determined, they can be used to determine the density or specific gravity of the fluid. As described above, this technique is more specifically illustrated and described in U.S. Pat. No. 4 956 793. Of course, these parameters can be determined by other means if such are desirable in other applications.

Once k and $c_p$ or $c_{pv}$ of a gas or fluid are known, flow correction factors in the form of simple, constant flow-independent factors for the fuel can be calculated and used. The flow correction factors have been developed to compensate mass or volumetric flow measurements for changes in fluid temperature, pressure, and/or composition. In other words, once k and $c_p$ of a fluid or gas or fuel is known, its true volumetric, mass and energy flows can be determined via the corrections:

$$G^* = G(k/k_0)^{m1}(c_p/c_{p0})^{m2}(p_r/p_{r0})^{m3}(T/T_0)^{m4} \quad (7)$$

$$V^* = V(k/k_0)^{n1}(c_p/c_{p0})^{n2}(P_r/P_{r0})^{n3}(T/T_0)^{n4} \quad (8)$$

$$M^* = M(k/k_0)^{p1}(c_p/c_{p0})^{p2}(P_r/P_{r0})^{p3}(T/T_0)^{p4} \quad (9)$$

$$E^* = E(k/k_0)^{q1}(c_p/c_{p0})^{q2}(P_r/P_{r0})^{q3}(T/T_0)^{q4} \quad (10)$$

where the subscript "$_0$" refers to the calibration condition such as methane at $T_O$ and $p_0$ and the m, n, p, and q are optimized but constant exponents; $P_r$ in the Prandle Number and $G^*$ equals the corrected value of the sensor signal G, $V^*$ equals the corrected value for the standard volumetric flow V, $M^*$ equals the corrected value for the mass flow, and E, equals the corrected value for the energy flow, E. This technique of applying correction factors to the sensor signal, the mass flow, the volumetric flow and the energy flow are explained in greater detail in U.S. Pat. No. 4 941 348 and co-pending application Ser. No. 07/789,411 and which to any extent necessary is deemed incorporated by reference herein.

In the present invention, after thermal conductivity, k, and specific heat, $c_p$, have been determined for the fuel flowing through conduit 20, the independent variable, which may represent the heating value, H, of the fuel flowing through conduit 20, or other desired parameter, is determined by evaluating the polynomial of the form of equations 3 or 4 as follows:

$$Y_s = A_0 + A_1 k_s^{n1} c_{ps}^{m1} x_s^{p1} y_s^{q1} T_s^{r1} P_s^{s1} + A_2 k_s^{n2} c_p^{m2} x_s^{p2} y_s^{q2} T_s^{r2} P_s^{s2} + \ldots \quad (3)$$

$$= \Sigma_i A_i k_s^{ni} c_{ps}^{mi} x_s^{pi} y_s^{qi} T_s^{ri} P_s^{si} \quad (4)$$

where dependent variable, $Y_s$, represents any one of higher heating value, H; oxygen demand, D; Wobbe Index, Wo; relative density or specific gravity, ρ; absolute density $ρ_a$; inerts, I; compressibility factor, Z; critical compression ratio, $R_c$; viscosity, η; etc.

$A_0, A_1 \ldots A_i$ are constants or coefficients, $n_i, m_i, P_i, q_i, r_i, s_i$ are exponents of values from −20 to 20, including zero, with the number of terms, i, ranging from 1 to 15, $k_s$ and $c_{ps}$ represent their values at a predetermined condition, which could be 60° F. 0° C., 15° C. or any other arbitrarily chosen temperature and pressure, $x_s$ represents dk/dT at the reference condition, $Y_s$ represents $dc_p/dT$ or $c_{pvT1}/c_{pvTs}$ at a reference condition, $T_1 \neq T_s$ (the units of $c_p$ are typically energy per unit of mass or mole and per ΔT, while those of $c_{pv}$ are typically energy per volume and per ΔT), $T_s$ represents temperature at said reference condition, $P_s$ represents absolute pressure at the reference condition. in which the needed values of $k_s$ and $c_{ps}$ are determined as in $$k_s = a_0 + a_1 k_{ti}^{m1} - b_2(k_{t2} - k_{t1})(t_1 - t_s)/(t_2 - t_1) \quad (5)$$

$$c_{ps} = b_0 + b_1 c_{pt}^{n1} - b_2(c_{pt2} - c_{pt1})(t_1 - t_s)/(t_2 - t_1) \quad (6)$$

where a and are constants $t_1$ and $t_2$ are temperatures or pressures in a desired range $t_s$ is the standard temperature or pressure.

The use of equations (3) and (4) has been found to be very effective in obtaining improved accuracy in determining H or D, even outside of the range of normally provided natural fuel gases. A comparison between actual and computed heating values of 78 natural and 22 test gases using the relationship of equation (3) or (4) to determine H is illustrated in FIG. 4 in which points A-V represent the 22 test gases and the other points, the 78 natural gases tested. In that comparison, the standard computation or algorithm error, $E_A$, was 2.1 Btu/ft³ or 0.21%. This includes such combinations as ethane or propane and air which have been used as test gases or as "peak shaving" gases when the demand for pipeline gas exceeds the supply. In practice, of course, the reliability or total error in H or D is not only influenced by the error of the algorithm, $E_A$, but also by its sensitivity, S, to experimental errors in the input parameters k, $c_p$, and their temperature derivatives. The improved algorithm can still result in large total errors, $E_T$, if k and $c_p$ are not measurable with small experimental errors, $E_x$, e.g. below 0.1%, because the total error is given by $$E_T = S \times E_x + E_A. \quad (11)$$

A comparison between the actual measured and computed heating values of 78 natural and 22 test gases yielded a standard computed error of 1.88 Btu/ft³ or −0.18%.

It is well known that hydrocarbon-type fuels combine with oxygen under a constant (hydrocarbon-independent) rate of heat release. The heat released by combustion is about 100 Btu/ft³ of reacted $O_2$ of air at 760 mmHg and 20° C. or (68° F.). This is exactly true for fuel with an atomic hydrogen/carbon ratio of 2.8 and a heating value of 21300 Btu/lb of combustibles and is true to within an error of less than +/−0.20% for other alkane hydrocarbons from methane to propane (i.e. $CH_4$, $C_2H_6$ and $n-C_3H_8$).

For example, in order to achieve stoichiometric (zero excess air) combustion, the mixture would be one cubic foot of air for each 100 Btu of fuel (e.g. about 0.1 cubic foot of $CH_4$). A more typical mix would be 10% to 30% excess air which would require 1.1 to 1.3 cubic feet of air for each 100 Btu of fuel. This would be a typical mixture because residential appliances typically operate in the 40–100% excess air range while most commercial combustion units operate between 10 and 50% excess air.

Although the present invention has been described with reference to fuels with hydrocarbon constituents, the present invention can be used to control the fuel-to-air ratio for other fuels. Each fuel used in combustion requires or demands a certain amount of oxygen for complete and efficient combustion (i.e. little or no fuel or oxygen remaining after combustion). The amount of oxygen required by each fuel is the oxygen demand value D for that fuel. D, then, is defined as units of moles of $O_2$ needed by each mole of fuel for complete combustion. For example, the $O_2$ demand for $CH_4$, $C_2H_6$, $C_3H_8$, CO, $H_2$ and $N_2$ is $D_f$=2, 3.5, 5.0, 0.5, 0.5 and 0 respectively.

Air is used to supply the oxygen demand of the fuel during combustion. In other words, fuel is an oxygen consumer and air is an oxygen supplier or donator during combustion. The $O_2$ donation $D_0$, is defined as the number of moles of $O_2$ provided by each mole of air. The single largest factor which influences $D_0$ is the humidity content of the air. Absolutely dry air has a value of $D_0$=0.209, while normal room temperature air with 30% relative humidity (or 1 volume % or 0.01 mole fraction of $H_2O$) has a value of $D_0$=0.207.

Therefore, one type of combustion, efficiency or fuel/air ratio control can be accomplished by: 1) correlating the sensed k and $c_p$ of the fuel to its oxygen demand value D, 2) correlating a second set of sensed k and $c_p$ of the air to its oxygen supply, 3) multiplying $D_0$/D by the desired excess air factor, e.g. A=1.3 (30% excess air), and 4) comparing the (set point) $AD_0$/D to the measured ratio of standard or actual c but equal T, P of fuel and air) volume flow $V_{air}/V_{fuel}$ and 5) adjusting $V_{air}$ and/or $V_{fuel}$ to match $AD_0$/D.

Figure 7:
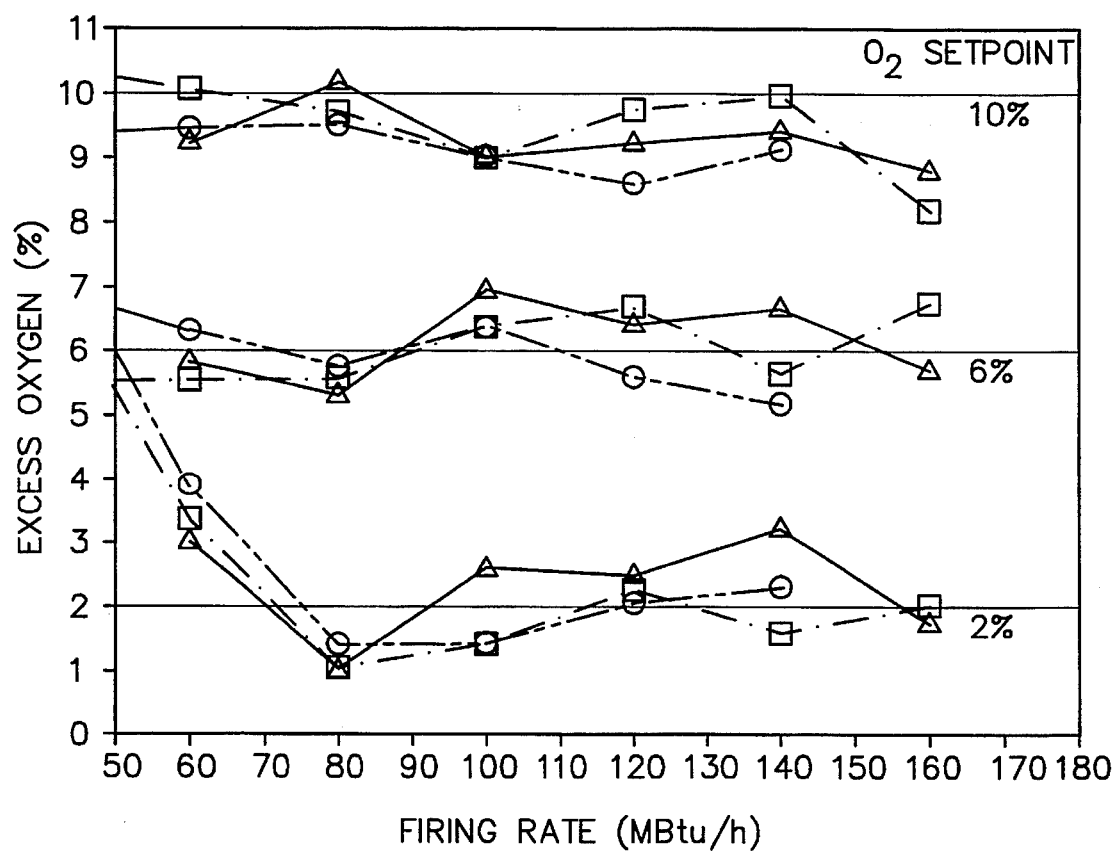
FIG. 7 is a graphical representation of actual excess oxygen control performance at three set points for three different fuel gases over a wide range of burner firing rates based on the invention.

Excess air control performance of a burner in terms of percent excess oxygen based on the relationship of the invention is shown in FIG. 7 for the three different fuel gases at each of three different excess oxygen set points. The illustrated results represent control parameters that were not corrected for relative humidity of air. The burners were operated over a relatively wide range of firing rate ratio, i.e. from 160 MBtu/h to 150 MBtu/h (turndown ratio >3:1) and maintained, for the most part, on excess oxygen correlation within 1% or less of the set point. As seen in FIG. 1, the firing rate responds to the demand for heat or steam; the sensors 26 and 24 determine the $O_2$ or air flow demand to satisfy the set excess air or $O_2$, and the air flow sensor 28 verifies that the blower 16 is providing that demand.

Heating value, H, or Wobbe Number, Wo, would typically be used in fuel for management systems either to achieve fuel gases within a desired range of Wo or to achieve an accurate method of billing customers, in view of the variability of the changed make up of the supply of fuel gases which results in variations of heating value and Wobbe Index. Having determined the higher heating value, the Wobbe Number or Index, Wo, can be derived from the higher heating value, H, and the density, ρ, according to the relation given above in equation (2) or Wo=H(ρ)$^{0.5}$.

The determination of ρ in absolute density units, as $ρ_a$, rather than as specific gravity in relation to air is also possible. The actual molar volume $V_M$ of the fuel of interest at the measurement temperature and pressure is determined based on $$V_M = c_p/c_{pv} \quad (12)$$

This, in turn, is related to that at a standard temperature and pressure (0° C., 1 Atmosphere), $V_{MO}$ and the actual gas density $ρ_a$ is determined from $$ρ_a = ρ_o V_{MO}/V_M \quad (13)$$

where $ρ_0$ is a constant equal to the density of the air at standard conditions (0° C. and 1 Atmosphere), $ρ_A$ is the absolute specific gravity, $V_{MO}$ is a constant equal to the molar volume at standard temperature air pressure, i.e. ~22.4 l/m and $V_M$ is the actual molar volume at the temperature and pressure of measurement.

Figure 5:
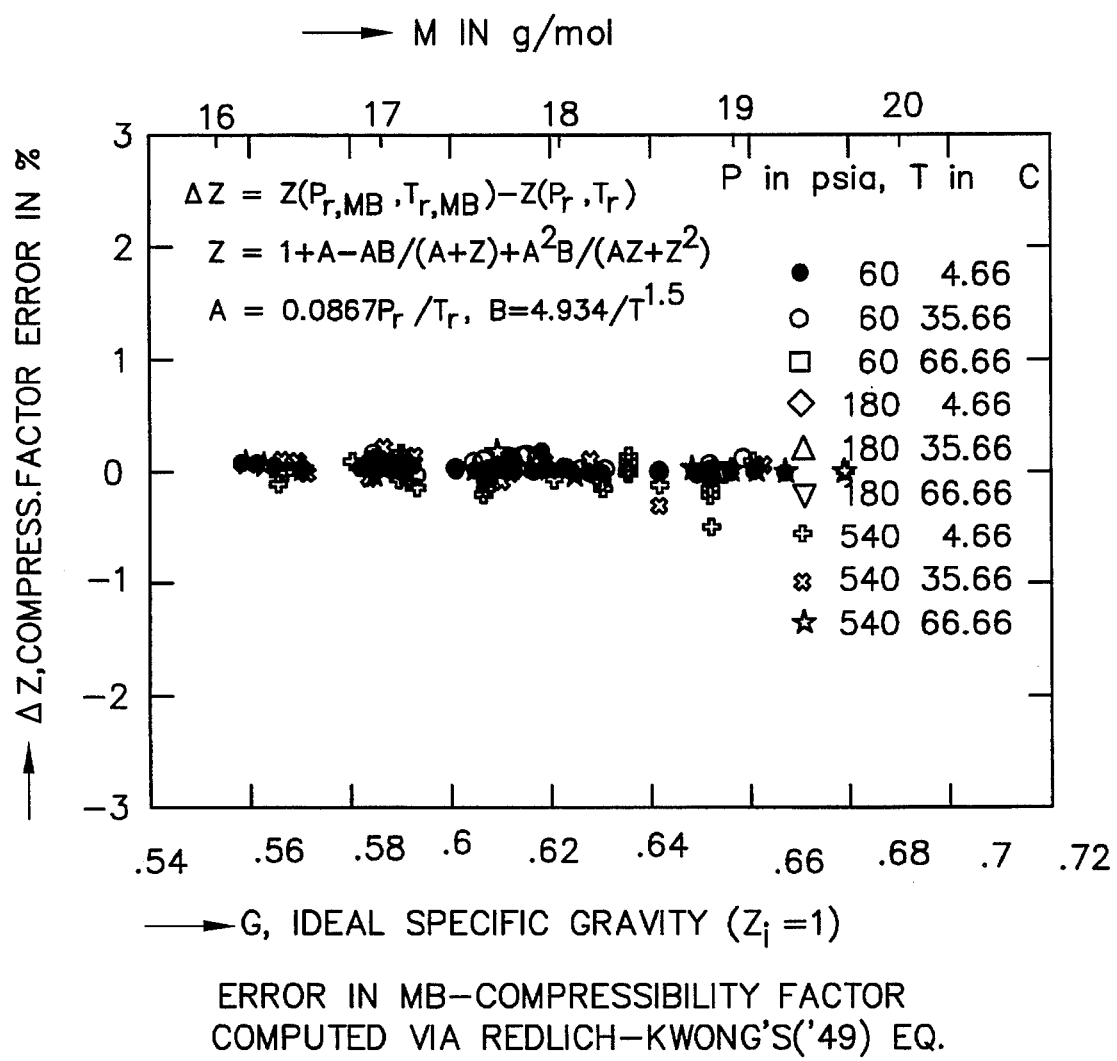
FIG. 5 is a graphical representation of the error in the determination of the compressibility factor for a range of gases using the relationship of equation 14 over a range of temperatures and pressures.

With respect to the measurement of the compressibility factor, Z, values can either be determined directly as a function of of k, $c_p$, x, y, . . . (see equation 4) or by first computing the pseudo-critical pressure and temperature, $P_{pc}$ and $T_{pc}$, via correlations, as described below. The known Redlich-Kwong equation may then be applied to find the compressibility, Z, by a few iterations:

$$Z = 1 + A - AB/(A+Z) + A^2 B/(AZ + Z^2) \quad (14)$$

where $A = 0.0867 \, P_r/T_r$, $B = 4.934/T_r^{1.5}$ and $P_r = P/P_{pc}$, $T_r = T/T_{pc}$ (reduced pressure and temperature) FIG. 5 illustrates the correlation and error of this microbridge-based approach. The simulated microbridge sensor values of $Z_{MB}$ were obtained via equation (14) by using k and $c_p$ values computed for 78 natural gases from their known composition which would simulate and represent the result of a microbridge sensor-based system (because of the microbridge-measured values of k and $c_p$); "correct" values of Z were obtained by computing $T_{pc}$ and $P_{pc}$ via $$T_{pc} = \Sigma_i x_i T_c, \; Z_{pc} = \Sigma_i x_i Z_c, \; V_{pc} = \Sigma_i x_i V_c \quad (15)$$

and $$P_{pc} = Z_{pc} R_o T_{pc}/V_{pc} \quad (17)$$

which is also known as the combination rule of Prausnitz and Gunn; the difference $$\Delta Z = Z_{MB}(P_{r,MB}, T_{r,MB}) - Z(P_r, T_r) \quad (17)$$

is plotted in FIG. 5 for the 78 gases, each taken at a matrix of three temperatures and three pressures. As shown, the correlation errors at high pressure are largest, but still within about ±0.5%. The total error would also be influenced by any experimental errors associated with the k and $c_p$ measurements.

Figure 6:
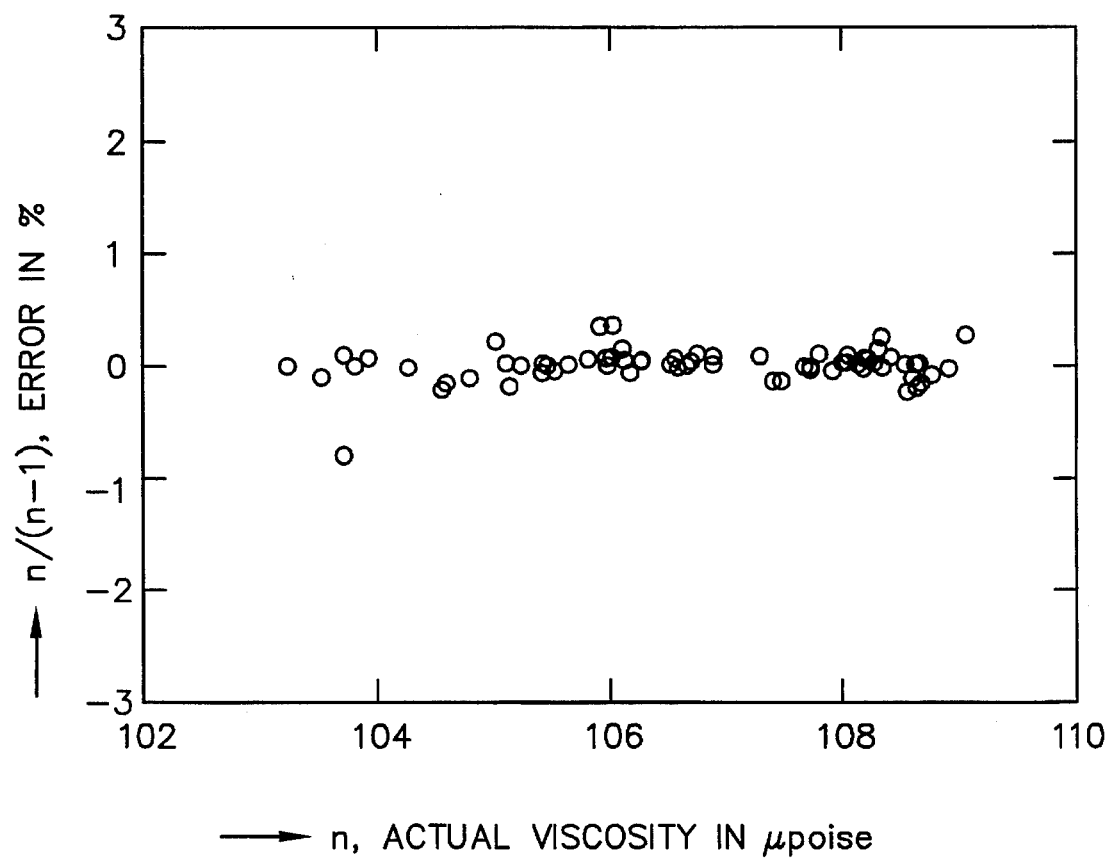
FIG. 6 is a graphical representation of the error in the determination of the actual viscosity of the 78 natural gases based on the relationship of the invention.

Viscosity, like compressibility, can also be related to k and $c_p$ by means of equations (3) and (4). This is illustrated by FIG. 6 in which the error in the measurement of actual viscosity is plotted for the 78 natural gases used in FIGS. 3–5.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications both as to equipment and procedure details can be accomplished without departing from the scope of the invention itself.

What is claimed is:

1. A method for determining thermophysical or thermochemical property values of a natural or other hydrocarbon-based gaseous fuel gas with microbridge type sensors, comprising the steps of:

applying the fuel to a static microbridge type sensor to obtain the thermal conductivity value of the fuel wherein the microbridge type sensor is fluidly coupled to receive the fuel and provide a signal value, thermal conductivity, k, of the fuel;

applying the fuel to a static microbrid type sensor to obtain the specific heat value of the fuel wherein the microbridge type sensor is fluid coupled to receive the fuel and provide a signal value, specific heat, $c_p$, of the fuel;

correcting the values of signals k and $c_p$ through the use of a plurality of measured sensor signal values k and $c_p$ taken at different temperatures so as to be able to process these values to obtain corresponding values at reference conditions for the fuel;

processing the plurality of measured different temperature values of $c_p$ to obtain a value for $dc_p/dT$ at the said reference condition of $c_{ps}$, processing the plurality of measured different temperature values of $k_s$ to obtain a value for $dk/dT$ at the said reference condition of $k_s$, processing in a processor the values obtained in the previous steps to obtain the desired property of the fuel according to a relationship selected from:

$$Y_s = A_0 + A_1 k_s^{n1} c_{ps}^{m1} x_s^{p1} y_s^{q1} T_s^{r1} P_s^{s1} + A_2 k_s^{n2} c_{ps}^{m2} x_s^{p2} y_s^{q2} T_s^{r2} P_s^{s2} + \ldots$$

$$= \Sigma_i A_i k_s^{ni} c_{ps}^{mi} x_s^{pi} T_s^{ri} P_s^{si}$$

where $Y_s$ represents a thermophysical or thermochemical parameter of interest selected from any of the higher heating value, H; oxygen demand, D; Wobbe Index, Wo; relative density or specific gravity, $\rho$; absolute density, $\rho_a$; inerts, I; compressibility factor, Z; critical compression ratio, $R_c$; viscosity, $\eta$;

$A_0, A_1 \ldots A_i$ are constants or coefficients, $n_i, m_i, p_i, q_i, r_i, s_i$ are exponents of values from −20 to 20, including zero, with the number of terms, i, ranging from 1 to 15, $k_s$ and $c_{ps}$ represent their values at a predetermined reference condition of temperature and pressure, $x_s$ represents $dk/dT$ at the reference condition, $Y_s$ represents $dc_p/dT$ at a reference condition, $T_s$ represents temperature at the reference condition, $P_s$ represents absolute pressure at the reference condition.

2. The method of claim 1 wherein $k_s$ and $c_{ps}$ are determined by the expressions:

$$k_s = a_0 + a_1 k_{ti}^{m1} - a_2(k_{t2} - k_{t1})(T_1 - T_s)/(T_2 - T_1)$$

$$c_{ps} = b_0 + b_1 c_{pt}^{n1} - b_2(c_{pt2} - c_{pt1})(T_1 - T_s)/(T_2 - T_1)$$

where $a_i$ and $b_i$ are constants m1 and n1 are exponents $T_1$ and $T_2$ are temperatures in a desired range $T_s$ is the reference temperature.

3. The method of claim 1 wherein the relation is fitted individually to a series of limited ranges of Values of the parameter of interest which include two or more ranges, for any of the involved parameters to thereby optimize the relation for each given range.

4. The method of claim 2 wherein the relation is fitted individually to a series of limited ranges of values of the parameter of interest which include two or more ranges, for any of the involved parameters to thereby optimize the relation for each given range.

5. The method of claim 2 comprising the additional steps of:

relating the variable $Y_s$ to the oxygen demand of the fuel D; and controlling the firing of one or more burners by sending control signal values from the processor based on the value of $Y_s$ and of D to a controller that controls the firing of the burner(s) based on a preselected set point of the controller and based on an amount of excess oxygen.

6. The method of claim 2 wherein the parameter of interest is the higher heating value.

7. The method of claim 2 wherein the absolute density $\rho$ is derived from the values of $c_p$ and $c_{pv}$ from the relation $$\rho_A = \rho_0 V_{MO}/V_H$$

where $\rho_0$ is the density of the air at standard conditions (0° C. and 1 Atmosphere), $\rho_A$ is the density at actual-conditions of P and T, absolute specific gravity, $V_{MO}$ is a constant equal to the molar volume at standard temperature air pressure, i.e. ~22.4 l/m and $V_M = c_p/c_{pv}$ is the actual molar volume at the temperature and pressure of measurement.

8. The method of claim 2 wherein the parameter of interest is compressibility, Z.

9. The method of claim 8 wherein the Z determined is $Z_{MB}$ and wherein this value is corrected by the further step of applying the difference $$\Delta Z = Z_{MB}(P_{r,MB}, T_{r,MB}) - Z(P_r, T_r)$$

where $P_r = P/P_{p/c}$ $T_r = T/T_{pc}$ (Reduced temperature and pressure MB indicates derived from measurement).

10. The method of claim 2 further comprising the step of: converting each derived signal Y into an electrical signal in the form of a fuel gas regulation signal.

11. The method of claim 2 including the step of automatically periodically repeating the determination of $Y_s$ for the parameter of interest.

12. The method of claim 2, further comprising the step of: transmitting the derived signals for $Y_s$ of the parameter of interest to at least one of display means and recording means.

13. The method of claim-11, further comprising the step of: transmitting the derived signals for $Y_s$ of the parameter of interest to at least one of display means and recording means.

14. A method of determining thermophysical or thermochemical characteristics of a fuel gas of interest flowing through a fluid conduit comprising the steps of:

(a) conducting at least a partial stream of the fuel gas through a sensor chamber having one or more sensors in contact with the fuel gas;

(b) generating a first electrical signal indicative of temperature of the fuel gas;

(c) generating a second electrical signal at a sensor in contact with the fuel gas, the first electrical signal being representative of a first fuel gas quality, the first fuel gas quality comprising one of the thermal conductivity and specific heat;

(d) conducting the first electrical signal to a computing means;

(e) generating a third electrical signal at a sensor in contact with the fuel gas, the third electrical signal being representative of a second fuel gas quality, the second fuel gas quality comprising one of the thermal conductivity and specific heat, the second gas quality comprising a different one of the fuel gas qualities than the first gas quality;

(f) conducting the second electrical signal to the computing means;

(g) repeat steps (a)–(f) at a different fuel temperature; and (h) using the computing means to derive a signal for at least one of measurement and regulation using the received first and second electrical signals representative of the first fuel gas quality and second fuel gas quality, respectively, as a measure for at least one of the desired parameters according to a relationship $$Y_s = A_0 + A_1 k_s^{n1} c_{ps}^{m1} x_s^{p1} y_s^{q1} T_s^{r1} P_s^{s1} + A_2 k_s^{n2} c_p^{m2} x_s^{p2} y_s^{q2} T_s^{r2} P_s^{s2} + \ldots$$

$$= \Sigma_i A_i k_s^{ni} c_{ps}^{mi} x_s^{pi} y_s^{qi} T_s^{ri} P_s^{si}$$

where $Y_s$ represents a thermophysical or thermochemical parameter of interest selected from any one of higher heating value, H; oxygen demand, D; Wobbe Index, Wo; relative density or specific gravity, $\rho$; absolute density $\rho_a$; inerts, I; compressibility factor, Z; critical compression ratio, $R_c$; viscosity, $\eta$;

$A_0, A_1 \ldots A_i$ are constants or coefficients, $n_i, m_i, p_i, q_i, r_i, s_i$ are exponents of values from −20 to 20, including zero, with the number of terms, i, ranging from 1 to 15, $k_s$ and $c_{ps}$ represent their values at a predetermined reference condition of temperature and pressure, $x_s$ represents dk/dT at the reference condition, $y_s$ represents $dc_p/dT$ or $c_{pvT1}/c_{pvTs}$ ($T_1 \neq T_s$) at a reference condition, $T_s$ represents temperature at the reference condition, $P_s$ represents absolute pressure at the reference condition.

15. The method of claim 14 wherein $k_s$ and $c_{ps}$ are determined by the expressions:

$$k_s = a_0 + a_1 k_{tf} - a_2 (k_{t2} - k_{t1})(T_1 - T_s)/(T_2 T_1)$$

$$c_{ps} = b_0 + b_1 c_{pt}^{n1} - b_2 (c_{pt2} - c_{pt1})(T_1 - T_s)/(T_2 - T_1)$$

where $a_i$ and $b_i$ are constants m1 and n1 are exponents $T_1$ and $T_2$ are temperatures in a desired range $T_s$ is the reference temperature.

16. The method of claim 14 further comprising the step of: converting each derived signal Y into an electrical signal in the form of a fuel gas regulation signal.

17. The method of claim 14 including the step of automatically periodically repeating the determination of $Y_s$ for the parameter of interest.

18. The method of claim 14, further comprising the step of: transmitting the derived signals for $Y_s$ of the parameter of interest to at least one of display means and recording means.

19. The method of claim 14, further comprising the step of: transmitting the derived signals for $Y_s$ of the parameter of interest to at least one of display means and recording means.

20. A method for determining thermophysical or thermochemical property values of a natural or other hydrocarbon-based gaseous fuel gas comprising the steps of:

obtaining the thermal conductivity value of the fuel through the use of a static microbridge type sensor located so as to be closely coupled with the fuel and provide an output of a signal value, k, representative of the sensor perceived;

obtaining the specific heat value of the fuel through the use of a static microbridge type sensor located so as to be closely coupled with the fuel and provide an output of a signal value, $c_{pv}$, representative of the specific heat of the fuel coupled to said sensor;

correcting the values of signals k and $c_{pv}$ through the use of a plurality of measured sensor signal values k and $c_{pv}$ taken at different temperatures so as to be able to process these values to obtain corresponding values at reference conditions for the fuel;

processing the plurality of measured different temperature values of $c_{pv}$ to obtain a value for $c_{pvT1}/c_{pvTs}$ at the said reference condition of $c_{pvs}$, processing the plurality of measured different temperature values of $k_s$ to obtain a value for dk/dT at the said reference condition of $k_s$, processing in a processor the values obtained in the previous steps to obtain the desired property of the fuel according to a relationship selected from:

$$Y_s = A_0 + A_1 k_s^{n1} c_{ps}^{m1} x_s^{p1} y_s^{q1} T_s^{r1} P_s^{s1} + A_2 k_s^{n2} c_{ps}^{m2} x_s^{p2} y_s^{q2} T_s^{r2} P_s^{s2} + \ldots$$

$$= \Sigma_i A_i k_s^{ni} c_{ps}^{mi} x_s^{pi} T_s^{ri} P_s^{si}$$

where $Y_s$ represents a thermophysical or thermochemical parameter of interest selected from any of the higher heating value, H; oxygen demand, D; Wobbe Index, Wo; relative density or specific gravity, $\rho$; absolute density, $\rho_a$; inerts, I; compressibility factor, Z; critical compression ratio, $R_c$; viscosity, $\eta$;

$A_0, A_1 \ldots A_i$ are constants or coefficients, $n_i, m_i, p_i, q_i, r_i, s_i$ are exponents of values from −20 to 20, including zero, with the number of terms, i, ranging from 1 to 15, $k_s$ and $c_{ps}$ represent their values at a predetermined reference condition of temperature and pressure, $x_s$ represents dk/dT at the reference condition, $Y_s$ represents $c_{pvT1}/c_{pvTs}$ (T1≠Ts) at a reference condition, $T_s$ represents temperature at the reference condition, $P_s$ represents absolute pressure at the reference condition.

21. A device for producing a usable value indicator for indicating any of a number of gas properties including a thermophysical or thermochemical parameter of interest selected from any of: the higher heating value, H; oxygen demand, D; Wobbe Index, Wo; relative density or specific gravity, $\rho$; absolute density, $\rho_a$; inerts, I; compressibility factor, Z; critical compression ratio, $R_c$; viscosity, said device comprising:

a conduit for carrying a hydrocarbon-based fluid of interest and having a portion recessed from the fluid path of the conduit;

at least one sensor adapted to produce output signal values representative of both the specific heat and thermal conductivity of the hydrocarbon-based fuel, said at least one sensor fluidly coupled to said fuel, processing means for receiving the output signal values from the sensor; and conversion means operating in cooperation with the processing means for converting said output values to said value indicator signal.

22. A device as set forth in claim 21 wherein the value indicator signal is used as a control input to a fuel consumption device controller, which in turn is used to control the rate and amount of inputs to a fuel consumption device.

23. A device as set forth in claim 22 further comprising at least one flow-type sensor having a flow signal representative of the rate of flow of fuel past said flow-type sensor, wherein the flow signal is converted and corrected by said processor means using the corrected values of thermal conductivity and specific heat for the fuel to produce a corrected flow indication signal.

24. A device as set forth in claim 21 further comprising a temperature sensor coupled to the fuel and providing a temperature output signal to the processing means.

25. A device as set forth in claim 21 further comprising a pressure sensor coupled to the fuel and providing a pressure output signal to the processing means.

26. A device as set forth in claim 22 wherein said fuel consumption device is a combustion chamber.

* * * * *

UNITED STATES PATENT AND TRADEMARK OFFICE
CERTIFICATE OF CORRECTION

PATENT NO. : 5,486,107
DATED : January 23, 1996
INVENTOR(S) : ULRICH BONNE

It is certified that error appears in the above-indentified patent and that said Letters Patent is hereby corrected as shown below:

Column 11, Line 16, cancel "fluid" and substitute --fluidly--

Column 12, line 3, cancel "Values" and substitute --values--

Column 12, line 30, cancel "." after C

Column 12, line 32, cancel "-" after "actual"

Column 13, line 55 after $k_{ti}$ add $^{m1}$ so corrected equation reads:

$$k_s = a_o + a_1 k_{ti}^{m1} - a2(k_{t2} - k_{t1})(T_1 - T_s)/(T_2 - T_1)$$

Column 14, line 12, cancel "tbermophysical" and substitute --thermophysical--

Column 15, line 15, after "output" add --signal--

Signed and Sealed this

First Day of October, 1996

Attest:

BRUCE LEHMAN

*Attesting Officer*　　*Commissioner of Patents and Trademarks*